United States Patent
Lanham et al.

(10) Patent No.: US 9,541,439 B2
(45) Date of Patent: Jan. 10, 2017

(54) SENSOR HOUSING FOR A FLUID METER

(75) Inventors: Gregory Treat Lanham, Longmont, CO (US); Christopher A Werbach, Longmont, CO (US)

(73) Assignee: Micro Motion, Inc., Boulder, CO (US)

( * ) Notice: Subject to any disclaimer, the term of this patent is extended or adjusted under 35 U.S.C. 154(b) by 22 days.

(21) Appl. No.: 14/413,265

(22) PCT Filed: Jul. 24, 2012

(86) PCT No.: PCT/US2012/047974
§ 371 (c)(1),
(2), (4) Date: Jan. 7, 2015

(87) PCT Pub. No.: WO2014/018016
PCT Pub. Date: Jan. 30, 2014

(65) Prior Publication Data
US 2015/0192447 A1  Jul. 9, 2015

(51) Int. Cl.
*G01D 11/24* (2006.01)
*G01F 1/84* (2006.01)
*G01F 15/14* (2006.01)
*G01F 15/10* (2006.01)
*G01N 9/32* (2006.01)

(52) U.S. Cl.
CPC ............ *G01F 15/14* (2013.01); *G01D 11/245* (2013.01); *G01F 1/8409* (2013.01); *G01F 1/8486* (2013.01); *G01F 15/10* (2013.01); *G01N 9/32* (2013.01); *Y10T 29/49428* (2015.01)

(58) Field of Classification Search
CPC .......... G01D 11/24; G01D 11/245; G01F 1/84
USPC .......................................... 73/431, 861.355
See application file for complete search history.

(56) References Cited

U.S. PATENT DOCUMENTS

| 4,253,340 A * | 3/1981 | Schmoock ............... G01F 1/586 73/861.12 |
| 6,776,052 B2 * | 8/2004 | Crisfield ............... G01F 1/8409 73/861.354 |
| 8,286,503 B2 * | 10/2012 | Neuburger ............... G01F 15/14 73/861.12 |
| 2014/0083204 A1 * | 3/2014 | Hussain ................ G01F 1/8409 73/861.355 |

FOREIGN PATENT DOCUMENTS

| CH | EP 2187180 A2 * | 5/2010 | ............ G01F 1/588 |
| EP | 0092910 A1 * | 11/1983 | ............... G01F 1/42 |
| EP | 2187180 A2 | 5/2010 | |
| WO | 2012005735 A1 | 1/2012 | |

(Continued)

*Primary Examiner* — Michael A Lyons
*Assistant Examiner* — Jamel Williams
(74) *Attorney, Agent, or Firm* — The Ollila Law Group LLC

(57) ABSTRACT

A sensor system (30) including a sensor assembly (10) for a fluid meter (5) is provided. The sensor assembly (10) includes one or more fluid conduits (103A, 103B). The sensor assembly (10) also includes a case (101) surrounding at least a portion of the one or more fluid conduits (103A, 103B). The sensor system (30) also includes a case support (300). The case support (300) surrounds at least a portion of the case (101). The case support (300) includes one or more ribs (330) that extend along at least a portion of the case (101) and contact the case (101) at least when the case (101) deforms outward by a threshold amount.

16 Claims, 4 Drawing Sheets

(56) References Cited

FOREIGN PATENT DOCUMENTS

| | | | |
|---|---|---|---|
| WO | WO 2012005735 A1 * | 1/2012 | ........... G01F 1/8409 |
| WO | 2013060659 A1 | 5/2013 | |
| WO | 2013119198 A1 | 8/2013 | |

* cited by examiner

SENSOR HOUSING FOR A FLUID METER

TECHNICAL FIELD

The embodiments described below relate to, fluid meters, and more particularly, to a sensor system for a fluid meter with a case support surrounding at least a portion of the sensor assembly's case.

BACKGROUND OF THE INVENTION

Fluid meters such as, for example, densitometers, volumetric flow meters, and Coriolis flow meters are used for measuring one or more characteristics of substances, such as, for example, a density, a mass flow rate, a volume flow rate, a totalized mass flow, a temperature, and other information. Vibrating fluid meters include one or more conduits, which may have a variety of shapes, such as, for example, straight, U-shaped, or irregular configurations. The one or more conduits provide a primary containment of the measured fluid. The measured fluid may comprise a liquid, a gas, or a combination thereof. The fluid may include suspended particulates.

The one or more conduits have a set of natural vibration modes, including, for example, simple bending, torsional, radial, and coupled modes. The one or more conduits are vibrated by at least one driver at a resonance frequency in one of these modes, hereinafter referred to as the drive mode, for purposes of determining a characteristic of the substance. One or more meter electronics transmit a sinusoidal driver signal to the at least one driver, which is typically a magnet/coil combination, with the magnet typically being affixed to the conduit and the coil being affixed to a mounting structure or to another conduit. The driver signal causes the driver to vibrate the one or more conduits at the drive frequency in the drive mode. For example, the driver signal may be a periodic electrical current transmitted to the coil.

One or more pick-offs detect the motion of the conduit(s) and generate a pick-off signal representative of the motion of the vibrating conduit(s). The pick-off is typically a magnet/coil combination, with the magnet typically being affixed to one conduit and the coil being affixed to a mounting structure or to another conduit. The pick-off signal is transmitted to the one or more electronics; and according to well-known principles, the pick-off signal may be used by the one or more electronics to determine a characteristic of the substance or adjust the driver signal, if necessary.

Generally, the conduits as well as the driver and pick-offs are enclosed within a case. The case can provide numerous benefits, such as protection of the internal components as well as offer a secondary containment of the fluid if the fluid conduits develop a crack, for example. In order for the case to provide adequate secondary containment, the burst pressure (pressure at which a component fails) of the case should be at least as high as the operating pressure of the wetted fluid path (fluid conduits, manifold, flange, etc.). Many of the vibrating meters currently on the market have a wetted fluid path with a burst pressure of around 15,000 psi (1,034 bar); however, this number may vary depending on the material used for the wetted fluid path, the size of the meter, etc. A pressure rating for the wetted fluid path can then be assigned by a regulatory or safety agency based on the burst pressure or some other analytic equation. The secondary containment pressure rating typically includes a safety factor such that the rated pressure is below the actual burst pressure. For example, the American Society of Mechanical Engineers (ASME) currently implements a safety factor of about six to ten, depending on material properties, and the welding methods employed. Therefore, for a wetted fluid path having a burst pressure of around 15,000 psi (1,034 bar), the ASME pressure rating, assuming a safety factor of ten, is only 1,500 psi (103 bar). Due in part to the conservative pressure ratings of regulatory agencies, the burst pressure of the case must also increase drastically to provide approved secondary containment. This extreme increase in the case's burst pressure is problematic, especially when considering that the diameter of the case will always be much greater than the diameter of the wetted path components.

In order to understand how to increase the pressure rating of the case, the shape of the case can be simplified and characterized as a thin-walled, cylindrical-shaped component where the pressure within the case acts against the walls of the case creating a hoop stress. Hoop stress can be characterized by equation (1).

$$\sigma = \frac{P * ID}{2t} \qquad (1)$$

Where:
σ is the hoop stress;
P is the internal pressure;
ID is the internal diameter of the case; and
t is the case thickness.

Other stresses also exist, such as an axial stress, however hoop stress is typically the largest and therefore the most relevant to choosing a minimum thickness for a desired pressure rating. In many situations, the maximum allowable hoop stress is governed by regulatory agencies or other safety standards. Although the stresses experienced by the case are in reality more complicated than depicted by equation (1), the equation can provide a basic understanding of the main forces acting on the case. As can be appreciated from equation (1), one approach to maintaining an acceptable hoop stress while allowing for a higher pressure would be to decrease the internal diameter of the case. However, this approach is rarely possible without also decreasing the size of the fluid conduits. Another approach would be to increase the case thickness. The case is often formed from a metal such as stainless steel or carbon steel; although, other materials may be used, such as plastic. In relatively smaller meter sizes, i.e., less than about 1 inch (2.54 cm) internal conduit diameter, the standard case is often strong enough to provide adequate secondary containment for the fluid or alternatively, providing extra thickness to the steel case is reasonable and relatively inexpensive. As can be appreciated, as the conduit diameter increases, the case size typically also increases. Consequently, in vibrating meters that include conduit sizes greater than an approximately 1 inch (2.54 cm) internal diameter, the case's ability to contain the fluid pressure upon a conduit failure is diminished and increasing the thickness of the case has serious drawbacks. For example, some large flow rate vibrating meters can have cases with an internal diameter of 10 inches (25.4 cm) or more. Meters of this size are often seen in the oil and gas industry where secondary containment is becoming more important. Cases of this dimension often have a burst pressure of around 860 psi (59.3 bar), many times below the wetted path burst pressure of 15,000 psi (1,034 bar). With dimensions of this magnitude, the case would require a thickness of about 2 inches (5.08 cm), resulting in a case weight of over 2,000 pounds (908 kg) in order to have a burst pressure of 15,000 psi (1,034 bar). As can be appreciated, such an approach results in an excessive cost and weight for the vibrating meter case.

Due in part to the high cost and weight associated with increasing the thickness of the case, the cases used in the prior art for these larger meters were provided simply to protect the conduits and electrical components of the vibrating meter, but did not provide acceptable secondary fluid containment. This created a situation where a conduit failure would almost immediately result in a case failure. Due to ongoing safety concerns in addition to recent oil spills, chemical spills, and environmental concerns, there is increased demand to ensure that the cases of vibrating meters provide a secondary containment if a fluid conduit fails.

The embodiments described below overcome these and other problems and an advance in the art is achieved. The embodiments described below provide a sensor system with a case support surrounding at least a portion of a case of a sensor assembly. The case support can dramatically increase the burst pressure of the case while minimizing the added weight and effect on the case's vibrational frequencies. In some embodiments, the weight added by the case support can be reduced by forming the case support with a plurality of ribs extending from a center portion of the case. The ribs can increase the burst pressure of the case while minimizing the weight added.

SUMMARY OF THE INVENTION

A sensor system including a sensor assembly for a fluid meter is provided according to an embodiment. The sensor assembly includes one or more fluid conduits and a case surrounding at least a portion of the one or more fluid conduits. According to an embodiment, the sensor system further comprises a case support. The case support surrounds at least a portion of the case. According to an embodiment, the case support includes one or more ribs extending along at least a portion of the case.

A method for increasing a burst pressure of a sensor assembly for a fluid meter is provided according to an embodiment. The sensor assembly includes one or more fluid conduits. According to an embodiment, the method comprises a step of surrounding at least a portion of the one or more fluid conduits with a case. According to an embodiment, the method further comprises a step of surrounding at least a portion of the case with a case support including one or more ribs extending along at least a portion of the case. According to an embodiment, the method further comprises a step of contacting the case with the one or more ribs at least when the case deforms outward by a threshold amount.

ASPECTS

According to as aspect, a sensor system comprises:
a sensor assembly for a fluid meter including:
one or more fluid conduits;
a case surrounding at least a portion of the one or more fluid conduits; and
a case support surrounding at least a portion of the case, including one or more ribs extending along at least a portion of the case.
Preferably, the one or more ribs contact the case at least when the case deforms outward by a threshold amount.
Preferably, the case support is coupled to at least a portion of the case.

Preferably, the one or more ribs are coupled to an outer rim.
Preferably, the one or more ribs extend between a central hub and the outer rim.
Preferably, the one or more ribs extend along a face of the case.
Preferably, the case support comprises a first case support portion and a second case support portion coupled to one another around the case.

According to another aspect, a method for increasing a burst pressure of a sensor assembly for a fluid meter including one or more fluid conduits comprises steps of:
surrounding at least a portion of the one or more fluid conduits with a case;
surrounding at least a portion of the case with a case support including one or more ribs extending along at least a portion of the case; and
contacting the case with the one or more ribs at least when the case deforms outward by a threshold amount.
Preferably, the step of surrounding at least a portion of the case with the case support increases a deformation pressure of the case.
Preferably, the method further comprises a step of coupling the case support to the case.
Preferably, the step of surrounding at least a portion of the one or more fluid conduits comprises coupling a first case portion to a second case portion to create a case joint and wherein the step of coupling the case support to the case comprises coupling an outer ring to the case proximate the case joint.
Preferably, the step of coupling the case support to the case comprises coupling the one or more ribs extending between an outer rim and a central hub to the case.
Preferably, the step of surrounding at least a portion of the case comprises coupling a first case support portion to a second case support portion around the case.
Preferably, the method further comprises a step of heating the case support prior to surrounding at least a portion of the case.
Preferably, the method further comprises a step of allowing the case support to cool around the case to apply a compressive force against the case.

DETAILED DESCRIPTION OF THE INVENTION

FIGS. 1-3b and the following description depict specific examples to teach those skilled in the art how to make and use the best mode of embodiments of a sensor assembly. For the purpose of teaching inventive principles, some conventional aspects have been simplified or omitted. Those skilled in the art will appreciate variations from these examples that fall within the scope of the present description. Those skilled in the art will appreciate that the features described below can be combined in various ways to form multiple variations of the sensor assembly. As a result, the embodiments described below are not limited to the specific examples described below, but only by the claims and their equivalents.

Figure 1:
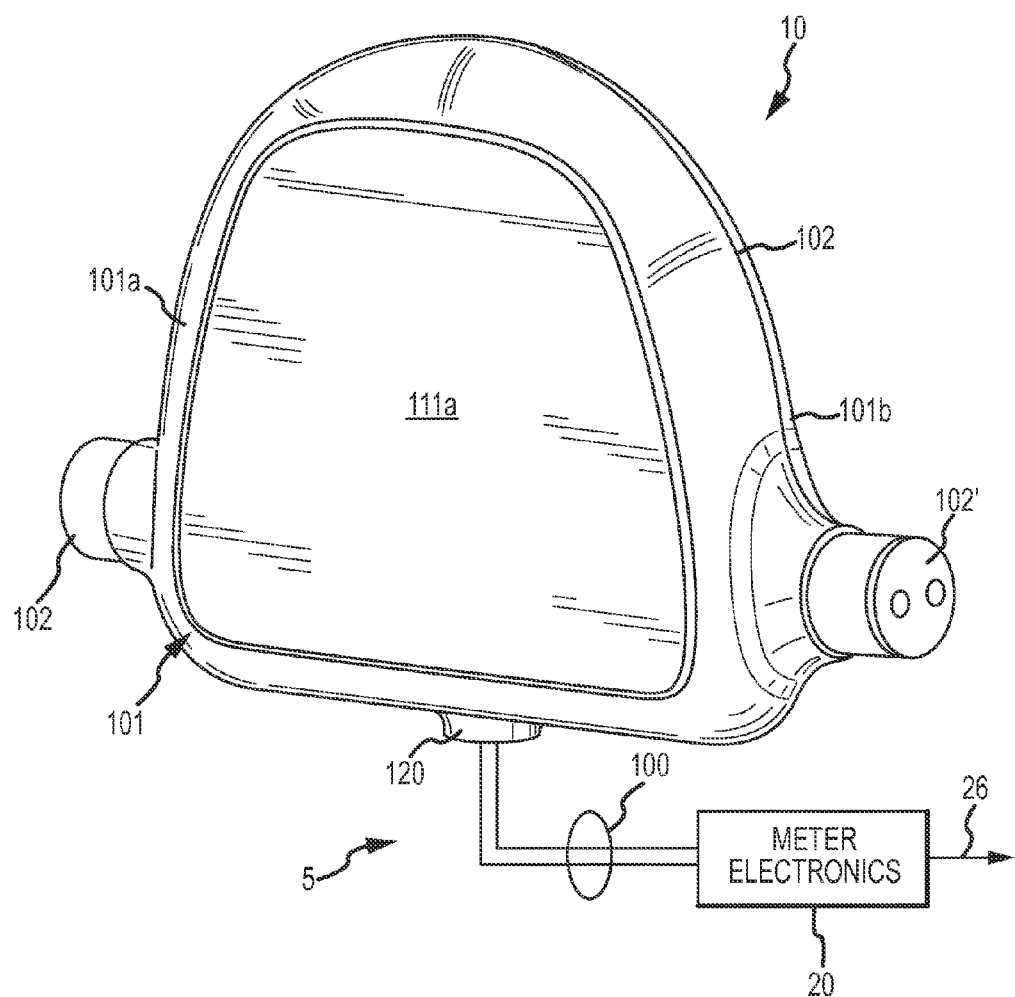
FIG. 1 shows a fluid meter according to an embodiment.
Figure 2:
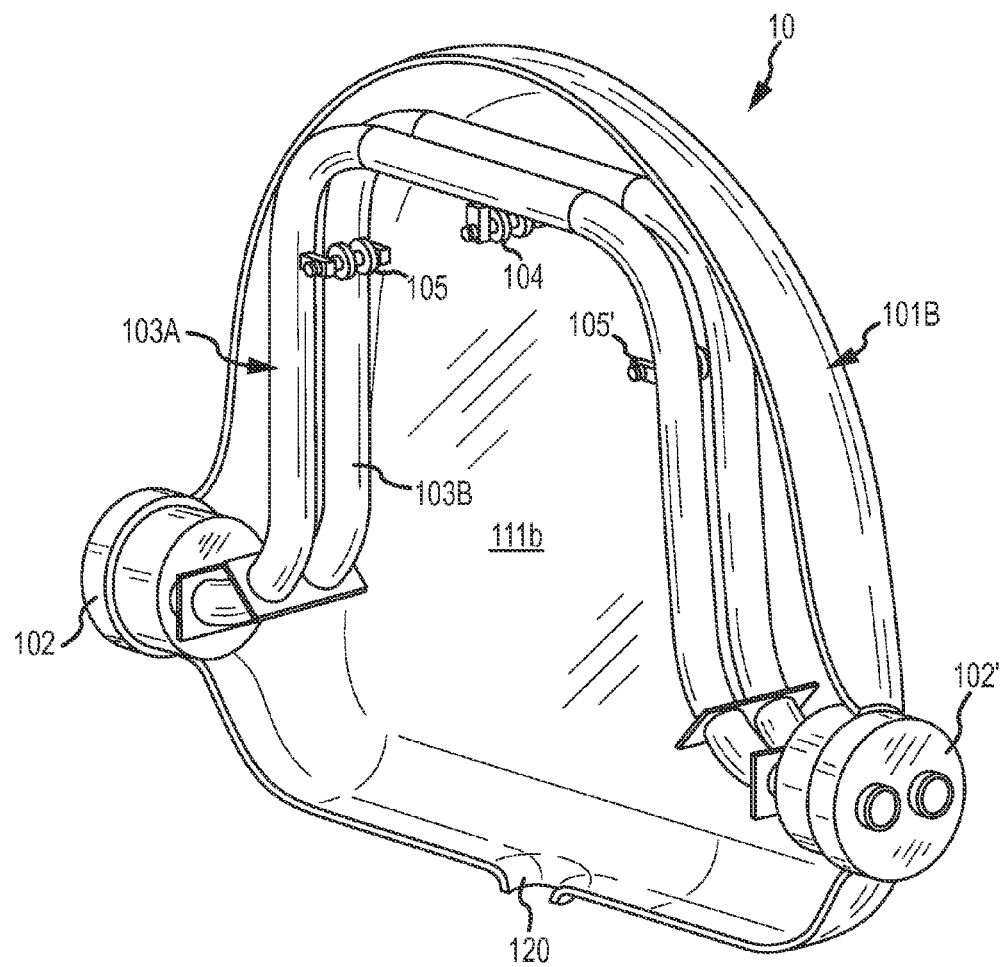
FIG. 2 shows the fluid meter with a portion of the case removed from the fluid meter's sensor assembly according to an embodiment.

FIGS. 1 & 2 show a fluid meter 5 according to an embodiment. The fluid meter 5 comprises a sensor assembly 10 and a meter electronics 20. The fluid meter 5 may comprise a Coriolis flow meter, a volumetric flow meter, a densitometer, etc. The fluid meter 5 may comprise a vibrating meter, or a non-vibrating meter. The sensor assembly 10 and the meter electronics 20 can be in electrical communication via leads 100, for example. The meter electronics 20 and the leads 100 are not shown in FIG. 2 in order to simplify the drawing. The meter electronics 20 can be in further communication with an external processing system or a user interface such as a computer via output 26. The fluid meter 5 can measure one or more characteristics of a substance, such as, for example, a fluid density, a mass flow rate, a volume flow rate, a totalized mass flow, a temperature, and other information over path 26.

According to an embodiment, the sensor assembly 10 includes a case 101. In FIG. 1, the case 101 is fully assembled and surrounds the fluid conduits 103A, 103B. However, in FIG. 2, the front portion 101a of the case 101 has been removed to show the interior components of the sensor assembly 10. As can be appreciated from FIG. 1, the front and back portions 101a, 101b can be coupled together along a case joint 102. According to an embodiment, the case joint 102 may comprise a weld joint, for example. However, other methods may be used to join the front and back portions 101a, 101b of the case 101, such as adhesives, brazing, etc. Extending between the case joint 102, each case portion 101a, 101b comprises a face 111a, 111b, respectively. In the embodiment shown, the faces 111a, 111b are generally flat and typically comprise the weakest portions of the case 101 and thus, are subject to the greatest deformation due to pressure, as is described in more detail below. Those skilled in the art will readily appreciate that while the case 101 is shown as comprising two portions 101a, 101b, in other embodiments, the case 101 may comprise more than two portions.

The sensor assembly 10 of the present example includes a pair of manifolds 102, 102'; a driver 104; pick-offs 105, 105'; and conduits 103A, 103B. The driver 104 and pick-offs 105, 105' are coupled to the fluid conduits 103A and 103B. The driver 104 is shown affixed to the fluid conduits 103A, 103B in a position where the driver 104 can vibrate a portion of the conduits 103A, 103B in a drive mode. The pick-offs 105, 105' are affixed to the conduits 103A, 103B in order to detect motion of the conduits 103A, 103B.

It should be appreciated by those skilled in the art that it is within the scope of the present invention to use the principles discussed herein in conjunction with any type of fluid meter, including fluid meters that lack the measurement capabilities of a Coriolis flow meter.

When the sensor assembly 10 is inserted into a pipeline system (not shown) which carries the substance, the substance enters sensor assembly 10 through the inlet manifold 102 where the total amount of material is directed to enter the conduits 103A, 103B, flows through the conduits 103A, 103B, and back into the outlet manifold 102' where it exits the sensor assembly 10.

As can be appreciated, the fluid within the conduits 103A, 103B is often at an elevated temperature and/or pressure and may be hazardous to the environment. Further, it is often difficult to detect cracks that may be developing in the fluid conduits 103A, 103B until it is too late. Therefore, the sensor assembly 10 often includes the case 101. Although the case 101 is shown in the figures as substantially completely surrounding the conduits 103A, 103B, in other embodiments, the case 101 may surround only a portion of the conduits 103A, 103B. For example, in some embodiments, the case 101 can surround just the portion of the conduits 103A, 103B where the driver 104 and pick-offs 105, 105' are located. As can be appreciated, the case 101 can include one or more feedthrus 120 for the leads 100.

The case 101 can surround the fluid conduits 103A, 103B along with other desired components of the sensor assembly 10. Often, the case 101 is made from a metal, such as stainless steel or carbon steel; however, other materials may be used. The case 101 is generally coupled to the manifolds 102, 102', which are more visible in FIG. 2. For example, the case 101 may be welded to the manifolds 102, 102'. In many embodiments, the case 101 comprises the two case portions 101a, 101b mentioned above, which are brought together to surround the fluid conduits 103A, 103B and welded or otherwise coupled together as discussed above.

According to an embodiment, the case 101 as shown in FIGS. 1 & 2 has a burst pressure that is lower than the burst pressure of the wetted fluid path. In other words, if a crack developed in the wetted fluid path, the case 101 would likewise fail due to pressure resulting in a potentially disastrous situation. Therefore, the case 101 shown in FIGS. 1 & 2 does not provide adequate secondary containment. Simply increasing the case's thickness in order to increase the case's burst pressure is often not a viable option as discussed above due to the excessive weight and cost associated with the approach.

Figure 3A:
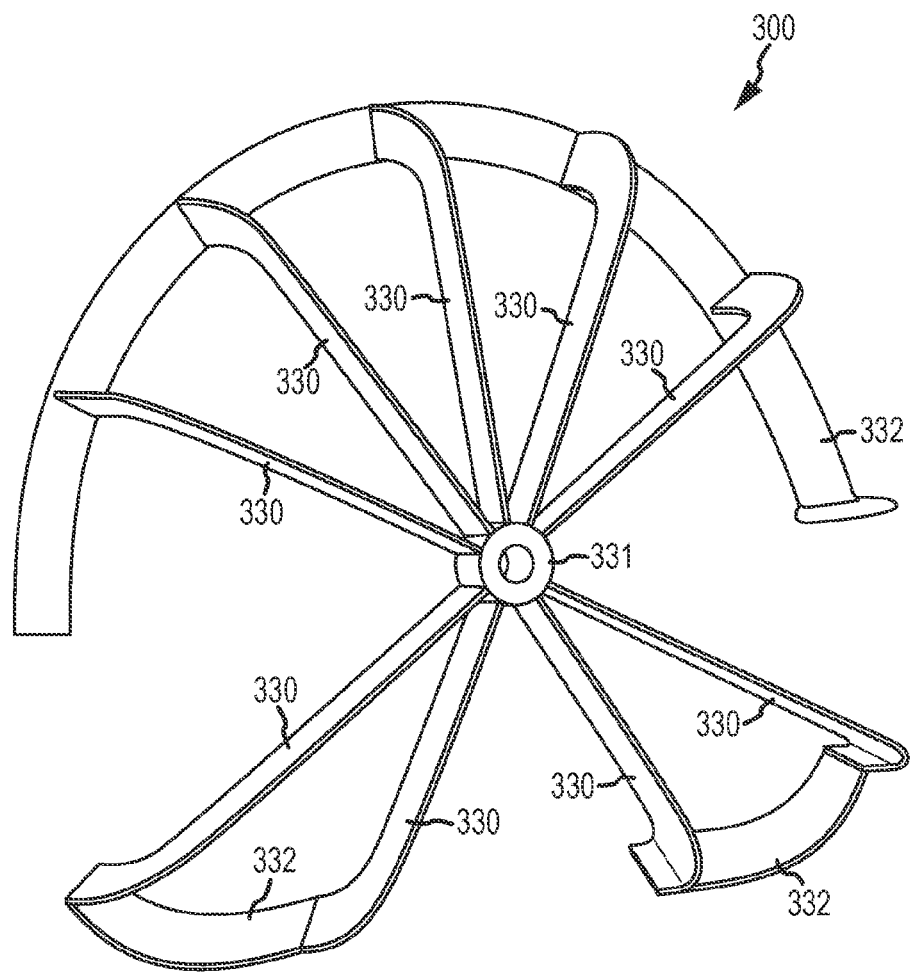
FIG. 3a shows a case support according to an embodiment.

FIG. 3a shows a case support 300 according to an embodiment. According to an embodiment, the case support 300 can be provided along with the sensor assembly 10 to provide a sensor system 30. As discussed in greater detail below, the case support 300 can comprise one or more ribs 330, which extend between a central hub 331 and an outer rim 332.

Figure 3B:
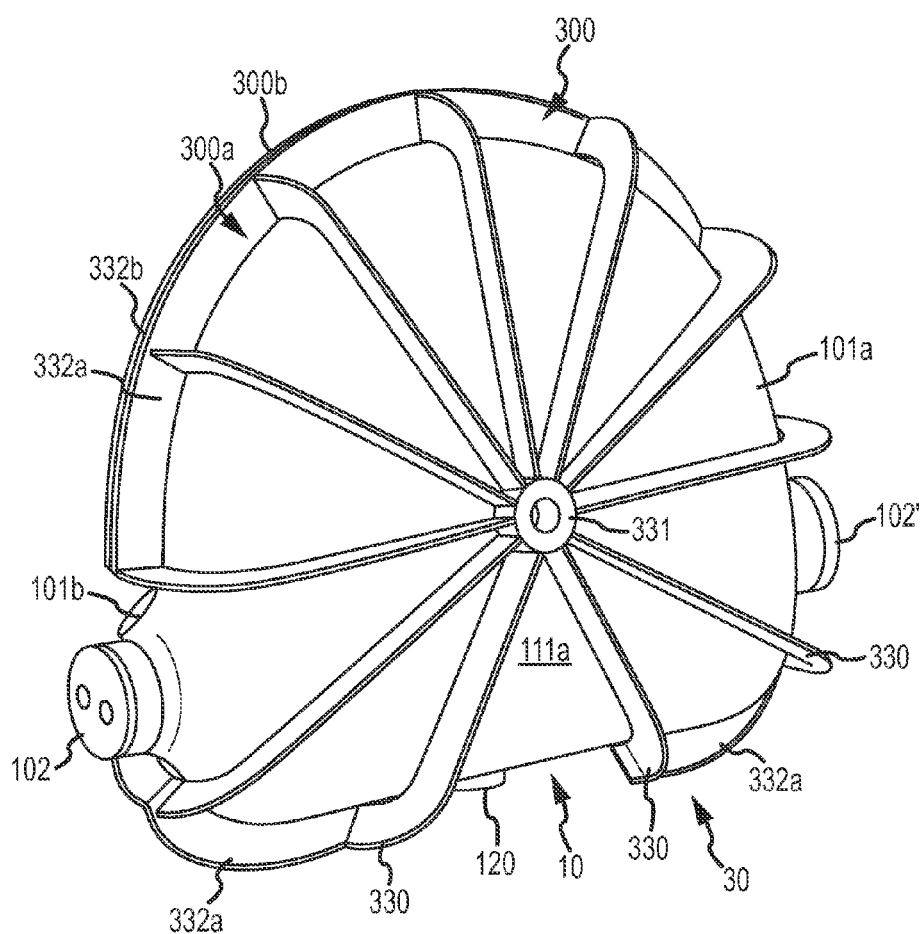
FIG. 3b shows the sensor assembly with a case support according to an embodiment.

FIG. 3b shows a sensor system 30 according to an embodiment. The sensor system 30 comprises the sensor assembly 10 and the case support 300. In the embodiment shown in FIG. 3, a case support 300 is provided. The case support 300 comprises an apparatus that at least partially surrounds the case 101 to restrict deformation of the case 101. According to an embodiment, the case support 300 can restrict deformation of the case 101 due to internal pressure, for example. The case support 300 can restrict case deformation by contacting the case 101 at least upon the case deforming outward by a threshold amount. As discussed below in some embodiments, the case support 300 may contact the case 101 at all times, even when the case 101 is not being deformed by the threshold amount.

In some embodiments, the case support 300 can comprise the same material used to form the case 101. For example, if the case 101 is made from carbon steel, the case support 300 can also be formed from carbon steel. However, other materials may be used and the particular material used to form the case support 300 may depend on the particular application and the desired increase in the pressure rating of the case 101.

According to an embodiment, the case support 300 can be sized and shaped to surround at least a portion of the case 101. In some embodiments, the case support 300 may only contact portions of the case 101 if the case 101 is deformed by a threshold amount due to the pressure within the case 101 exceeding a deformation pressure (pressure at which at least a portion of the case 101 deforms by a threshold amount). For example, in some embodiments, the case support 300 may not contact the faces 111a, 111b unless the faces 111a, 111b deform outward by a threshold amount. In such embodiments, the case support 300 may only be in contact with the case joint 102 during normal operation. According to another embodiment, the case support 300 can be suspended by an external element (not shown) such that when the case 101 is subject to less than the deformation pressure, no parts of the case support 300 contact the case 101.

According to an embodiment, the case support 300 can be coupled to at least a portion of the case 101. For example, the case support 300 can be welded or otherwise affixed to the case 101. In some embodiments, only some portions of the case support 300 may be coupled to the case 101 while other portions simply contact the case 101. For example, the case support 300 could be coupled to the case 101 proximate the case joint 102, but only contact the faces 111a, 111b of the case 101. Such a configuration may provide adequate support against deformation due to over pressurization while minimizing the required welding. However, in other embodiments, the case support 300 may simply contact the case 101 without being coupled to the case 101. For example, the case support 300 can comprise two or more portions 300a, 300b that can be coupled to one another and surround at least a portion of the case 101.

In the embodiment shown, the case support 300 comprises a first case support portion 300a and a second case support portion 300b. Although only a small section of the second case support portion 300b is visible, the two case support portions 300a, 300b are substantially identical and thus, a figure showing the second case support portion 300b is omitted for brevity.

Once the case 101 is assembled around at least a portion of the fluid conduits 103A, 103B, the first and second case support portions 300a, 300b can be brought together to surround at least a portion of the case 101. According to an embodiment, upon bringing the first and second case support portions 300a, 300b together, the two portions can be coupled to one another. For example, the case support portions 300a, 300b can be welded to one another. According to another embodiment, the two case support portions 300a, 300b may not be coupled to each other, but rather each of the case portions 300a, 300b can be coupled to the case 101. In yet another embodiment, the case support portions 300a, 300b may be coupled to each other as well as to the case 101.

According to another embodiment, the first and second case support portions 300a, 300b can be positioned around the case 101 prior to bringing the case around the fluid conduits 103A, 103B. For example, the first case support portion 300a could be coupled to the first case portion 101a and the second case support portion 300b could be coupled to the second case portion 101b. Subsequently, the case portions 101a, 101b can be brought into position to surround at least a portion of the fluid conduits 103A, 103B. The case portions 101a, 101b can then be coupled to one another. According to an embodiment, substantially simultaneously or subsequently, the two case support portions 300a, 300b could be coupled to one another as well. Therefore, in some embodiments, the order of assembly may not be important.

According to an embodiment, the case support 300 can include one or more ribs 330. In some embodiments, the one or more ribs 330 can join at a central hub 331. However, the one or more ribs 330 do not have to join at the central hub 331. According to the embodiment shown, the central hub 331 is positioned near the center of the face 111a of the case 101; however, in other embodiments, the central hub 331 may be located off-center of the face 111a of the case 101. For example, the central hub 331 could be positioned proximate a different location of the case 101 where the case's strength is at a minimum.

According to an embodiment, the one or more ribs 330 can extend between the central hub 331 and an outer rim 332. The outer rim 332 may not be continuous as shown in FIG. 3. In some embodiments, the one or more ribs 330 may be shaped to conform to the outer surface of the case 101 along the length of the ribs 330. The ribs 330 may or may not be coupled to the case 101. For example, in some embodiments, the central hub 331 and the outer rim 332 may be coupled to the case 101 while the ribs 330 simply contact the faces 111a, 111b of the case 101. In other embodiments, at least a portion of the ribs 330 can be coupled to the case 101 as well. In some embodiments, the one or more ribs 330 can contact a portion of the case 101, such as the faces 111a, 111b of the case 101 only if the case 101 deforms outward by a threshold amount. Upon contacting the one or more ribs 330, further deformation is restricted so as to increase a burst pressure of the case 101. It should be appreciated that while the ribs 330 primarily contact the faces 111a, 111b, the ribs 330 may contact other portions of the case 101.

If the faces 111a, 111b of the case portions 101a, 101b are thought of as large diaphragms, then the use of the ribs 330 can be better understood. As those skilled in the art will readily recognize, for a given material and thickness, the greater the surface area of a diaphragm, the less pressure required to deform the diaphragm. However, if reinforcing ribs are provided against a back surface of the diaphragm, then the effective surface area that can deform can be substantially reduced. This is because the portion of the diaphragm that abuts against the ribs is substantially prevented from deforming. Rather, multiple individual surface areas, which are much smaller, are provided that can withstand a higher pressure before deforming, i.e., the diaphragm has a higher deformation pressure.

Likewise, without the case support 300, the faces 111a, 111b comprise relatively large surface areas that can deform when acted upon by a threshold pressure. The threshold deformation pressure may be below the operating fluid pressure and thus, the case 101 will not provide adequate secondary containment. However, by providing the case support 300 with the one or more ribs 330, the surface area of the case 101 that can deform is separated between multiple individual smaller surface areas. The portions of the case 101 that abut the ribs 300 are substantially restricted from deforming and thus, below a threshold pressure, only the portions of the case 101 between the ribs 300 can deform. Consequently, a higher deformation pressure is required to deform the case portions 101a, 101b. Therefore, a higher pressure is required before a case failure.

Furthermore, the ribs 330 can be provided spaced apart, which results in a lower overall weight of the case support 300 compared to simply increasing the thickness of the case 101. In some embodiments, the lower weight results in less effect on the resonant frequencies of the case 101. As those skilled in the art will recognize, it is generally desirable to separate the case's resonant frequency from the drive frequency. Therefore, strengthening the case 101 while also minimizing the additional weight can result in an overall increase in the case's resonant frequency to above the drive frequency.

According to an embodiment, due to the one or more ribs 330 separating the available deformable surface area, the case support 300 can increase the burst pressure of the case 101. As mentioned above, the two case support portions 300a, 300b can be brought together around the case 101 and coupled together. According to some embodiments, the outer rims 332a, 332b can be welded together proximate the case joint 102. Therefore, with the outer rims 332a, 332b of the case support portions 300a, 300b joined together proximate the case joint 102, the case joint 102 can be additionally reinforced. As can be appreciated, if the outer rims 332a, 332b are contacting the case joint 102, a greater pressure will be required to deform and break the case joint 102 than prior art systems that do not include the case support 300.

For example, according to one finite element test, the case 101 was pressurized to approximately 15,000 psi (1,034 bar). Prior to providing the case support 300, portions of the case 101 deformed approximately 3.71 inches (9.42 cm). This deformation would be permanent and would likely fail resulting in a ruptured case 101. However, upon surrounding the case 101 with the case support 300 and being pressurized to the same 15,000 psi (1,034 bar) pressure, the maximum deformation detected was reduced to approximately 0.37 inches (0.94 cm). Therefore, the case support 300 resulted in a ten times reduction in the deformation of the case 101. This substantial reduction in the deformation can substantially increase the pressure rating of the case 101 as a much higher pressure would be required to permanently deform the case 101 or rupture the case 101. It should be appreciated that the particular values provided above are based on one test and case configuration and thus, should in no way limit the scope of the present embodiment.

According to an embodiment, in order to further increase the deformation pressure of the case 101, the case support 300 can be pre-stretched to increase the compression applied to the case 101. For example, the case support 300 could be heated, whereupon the case support 300 and in particular, the ribs 330 will expand based on the material's coefficient of thermal expansion. While heated, the case support 300 can be positioned around at least a portion of the case 101, such that at least a portion of the case 101 is surrounded by the case support 300. As the case support 300 cools, it will shrink around the case 101 and apply a compressive force against the case 101. In some embodiments, the compressive force can further increase the pressure required to deform the case 101.

The embodiments described above provide a sensor system 30 for a fluid meter 5 including a sensor assembly 10 and a case support 300. The case support 300 can surround at least a portion of the sensor assembly's case 101 in order to provide additional support against deformation due to excessive pressure. The case support 300 can thus, increase the burst pressure of the case 101 to provide adequate secondary containment. As those skilled in the art will readily recognize, the case support 300 may be added to existing sensor assemblies that are already in the field in order to provide suitable secondary containment for applications that currently lack secondary containment.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other sensor systems, and not just to the embodiments described above and shown in the accompanying figures. Accordingly, the scope of the embodiments described above should be determined from the following claims.

We claim:

1. A sensor system (30), comprising:
   a sensor assembly (10) for a fluid meter (5) including:
      one or more fluid conduits (103A, 103B);
      a case (101) surrounding at least a portion of the one or more fluid conduits (103A, 103B); and
   a case support (300) surrounding at least a portion of the case (101), including one or more ribs (330) extending along at least a portion of the case (101).

2. The sensor system (30) of claim 1, wherein the one or more ribs (330) contact the case (101) at least when the case (101) deforms outward by a threshold amount.

3. The sensor system (30) of claim 1, wherein the case support (300) is coupled to at least a portion of the case (101).

4. The sensor system (30) of claim 1, wherein the one or more ribs (300) are coupled to an outer rim (332a, 332b).

5. The sensor system (30) of claim 4, wherein the one or more ribs (330) extend between a central hub (331) and the outer rim (332a, 332b).

6. The sensor system (30) of claim 5, wherein the one or more ribs (330) extend along a face (111a, 111b) of the case (101).

7. The sensor system (30) of claim 1, wherein the case support (300) comprises a first case support portion (300a) and a second case support portion (300b) coupled to one another around the case (101).

8. A method for increasing a burst pressure of a sensor assembly for a fluid meter including one or more fluid conduits, comprising steps of:
   surrounding at least a portion of the one or more fluid conduits with a case; and
   surrounding at least a portion of the case with a case support including one or more ribs extending along at least a portion of the case.

9. The method of claim 8, further comprising a step of contacting the case with the one or more ribs at least when the case deforms outward by a threshold amount.

10. The method of claim 8, wherein the step of surrounding at least a portion of the case with the case support increases a deformation pressure of the case.

11. The method of claim 8, further comprising a step of coupling the case support to the case.

12. The method of claim 11, wherein the step of surrounding at least a portion of the one or more fluid conduits comprises coupling a first case portion to a second case portion to create a case joint and wherein the step of coupling the case support to the case comprises coupling an outer ring to the case proximate the case joint.

13. The method of claim 11, wherein the step of coupling the case support to the case comprises coupling the one or more ribs extending between an outer rim and a central hub to the case.

14. The method of claim 8, wherein the step of surrounding at least a portion of the case comprises coupling a first case support portion to a second case support portion around the case.

15. The method of claim 8, further comprising a step of heating the case support prior to surrounding at least a portion of the case.

16. The method of claim 15, further comprising a step of allowing the case support to cool around the case to apply a compressive force against the case.

\* \* \* \* \*